United States Patent
Biallas

(10) Patent No.: US 7,727,432 B2
(45) Date of Patent: Jun. 1, 2010

(54) PROCESS AND APPARATUS FOR QUALITY CONTROL OF A PROCESS FOR PRODUCING CONCRETE ARTICLES

(75) Inventor: Thorsten Biallas, Flensburg (DE)

(73) Assignee: Qavertec GmbH, Flensburg (DE)

( * ) Notice: Subject to any disclaimer, the term of this patent is extended or adjusted under 35 U.S.C. 154(b) by 0 days.

(21) Appl. No.: 12/086,819

(22) PCT Filed: Dec. 21, 2006

(86) PCT No.: PCT/EP2006/012394
§ 371 (c)(1), (2), (4) Date: Jun. 19, 2008

(87) PCT Pub. No.: WO2007/076958
PCT Pub. Date: Jul. 12, 2007

(65) Prior Publication Data
US 2008/0315463 A1 Dec. 25, 2008

(30) Foreign Application Priority Data
Dec. 21, 2005 (EP) .................................. 05028086

(51) Int. Cl.
G01B 11/02 (2006.01)
G01N 15/08 (2006.01)

(52) U.S. Cl. .................... 264/40.4; 264/40.1; 264/409; 73/38; 73/866; 425/169

(58) Field of Classification Search ............... 73/37, 73/38, 866; 264/40.1–40.5, 408, 409; 425/169
See application file for complete search history.

(56) References Cited

U.S. PATENT DOCUMENTS

| | | | |
|---|---|---|---|
| 3,578,372 A | * | 5/1971 | Schuler ..................... 294/64.1 |
| 4,979,390 A | * | 12/1990 | Schupack et al. .............. 73/38 |
| 5,766,538 A | * | 6/1998 | Kossmann .................. 264/407 |

FOREIGN PATENT DOCUMENTS

| | | |
|---|---|---|
| DE | 3628955 | 3/1988 |
| DE | 19519275 | 12/1995 |
| GB | 2179588 | 3/1987 |

OTHER PUBLICATIONS

International Application No. PCT/EP2006/012394, International Search Report mailed Mar. 15, 2007, 6 pgs.

* cited by examiner

Primary Examiner—Kat Wyrozebski
Assistant Examiner—Scott W Dodds
(74) Attorney, Agent, or Firm—Schwegman, Lundberg & Woessner, P.A.

(57) ABSTRACT

Methods and apparatus are presented for quality control of a process to produce concrete goods products. The quality control is effected on the basis of measurements that are carried out on the concrete goods products in an intermediate step of the process after shaping and compacting in the fresh concrete phase. Measurement values are determined on a test fresh concrete product from the intermediate step of the process, which measurement values comprise a measure of the bulk density and the gas permeability of the test fresh concrete product. Subsequently, an estimated value for a quality measure of the hardened concrete product is determined on the basis of a predetermined predictive model. The predictive model relates the measurement values of fresh concrete products from the intermediate step of the process to the quality measure of the corresponding hardened concrete products.

27 Claims, 1 Drawing Sheet

Figure 1:
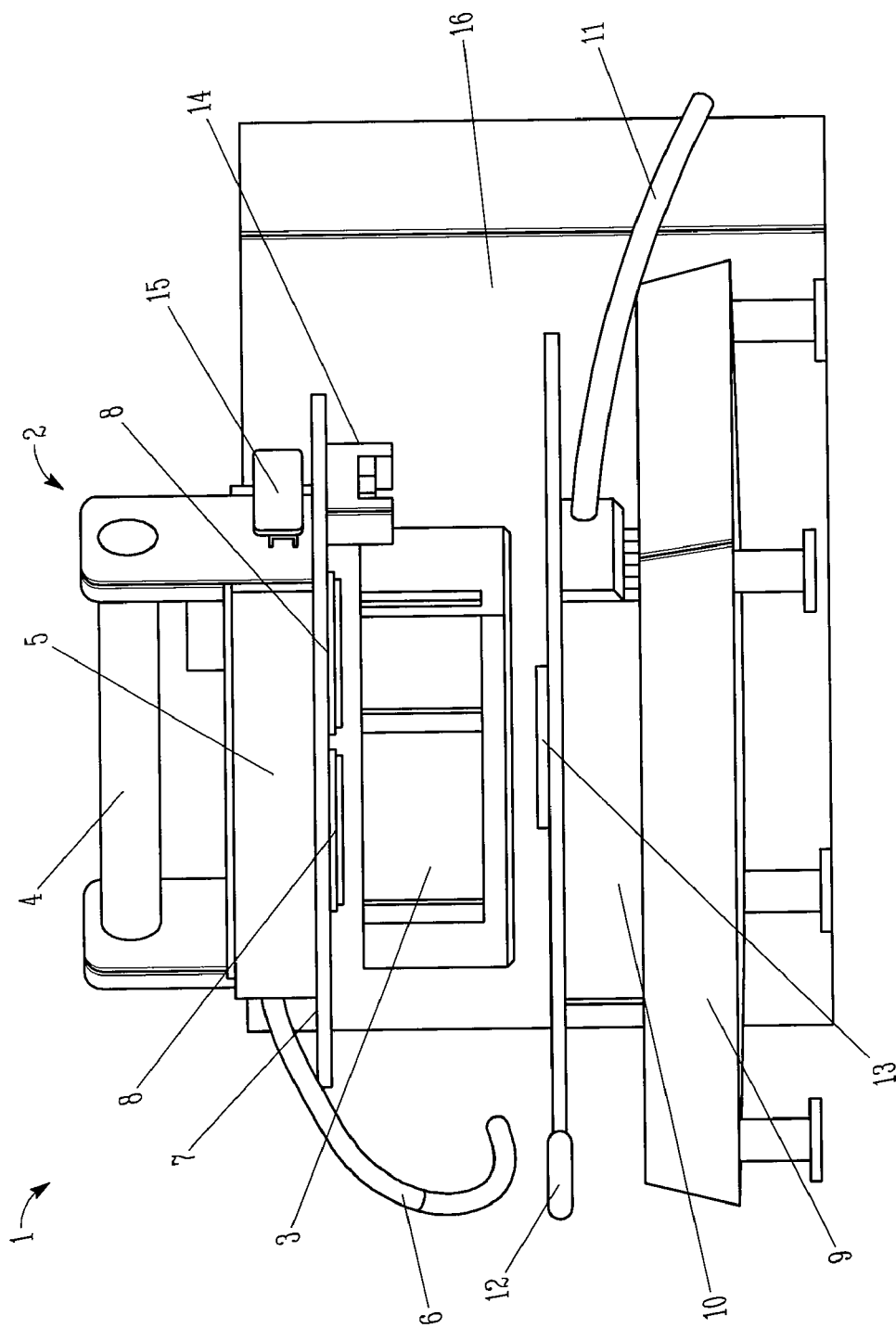

PROCESS AND APPARATUS FOR QUALITY CONTROL OF A PROCESS FOR PRODUCING CONCRETE ARTICLES

RELATED APPLICATIONS

This application is a nationalization under 35 U.S.C. 371 of PCT/EP2006/012394, filed Dec. 21, 2006 and published as WO 2007/076958 A1, on Jul. 12, 2007, which claimed priority under 35 U.S.C. 119 to European Patent Application No. 05028086.6, filed Dec. 21, 2005, which applications and publication are incorporated herein by reference and made a part hereof.

The present invention relates to a method and an apparatus for quality control of a process for producing concrete goods products (i.e. products which are concrete goods).

Concrete goods products are delivered as finished or precast products to their usage site, such as a construction site. One example for concrete goods products are paving stones. For the production of concrete goods products, at first concrete is mixed according to a predetermined recipe. Subsequently, the concrete is introduced into a machine, in which it is pressed into the shape of the desired concrete goods products and compacted in this process. In the case of paving stones a so-called stone shaping machine is used for pressing the paving stones. The green bodies resulting from the compaction process are still soft and workable. Subsequent to the compaction process the green bodies are arranged in a drying chamber for about one to two days, and are then stored for a further period of time. In the drying chamber and during the subsequent storage the concrete hardens, and in this manner the green bodies become finished or precast concrete goods products.

Roughly, the production process of the concrete goods products can be divided into two phases. The first phase until hardening of the concrete, i.e. the phase, in which the green bodies are still soft and workable, is generally referred to as fresh concrete phase. Correspondingly, the green bodies, which are still soft and workable, are referred to as fresh concrete products. Thus, the fresh concrete products are the fully pressed and compacted preforms of the finished concrete goods products. Following the fresh concrete phase is the hardened concrete phase, in which the concrete has hardened. Correspondingly, the finished or precast concrete goods products are also referred to as hardened concrete products. Thus, for the production of a particular concrete goods product, at first a corresponding fresh concrete product is produced from the concrete mixed in a suitable manner, which fresh concrete product becomes by hardening a hardened concrete product, that represents the desired concrete goods product.

Concrete goods products are regularly utilized in areas in which they are not only subjected to strong mechanical loads, but also to further external influences, such as water, snow, light, heat or frost. As construction or building materials they nevertheless have to have a long durability and, further, have to meet particular quality standards. Therefore, it is of great importance to be able to reliably determine the quality of the concrete goods products manufactured in the above manner. For example, often a strength value, the bulk density, the frost resistance or another quality measure of the finished concrete goods products is measured, in order to evaluate the quality of the production process and the concrete goods products produced thereby and in order to possibly make on the basis of this evaluation corrections on the process parameters.

In doing so, the difficulty arises that the hardening of the fresh concrete product to the hardened concrete product takes place over a relatively long period of time. The concrete achieves its strength by the clinker components of the cement, that forms a part of the concrete mix, crystallizing. Due to the crystallizing small crystal needles are formed that securely meshingly interengage with each other. However, because the crystal growth continues over a period of time of several months, the final strength is only achieved long after shaping and compacting, i.e. the production of the fresh concrete product. In DIN 1164/EN 1338 the standard strength as standardized quality measure for the hardened concrete products is defined as the strength that is achieved after 28 days under normal temperature and moisture conditions. Similarly, meaningful values of further quality measures, such as, for example, the bulk density or the frost resistance, are also only achieved after this period of time. Therefore, for quality control individual finished or precast test concrete goods products are usually checked with regard to their quality only after 28 days. Only then it is determined whether or not the concrete goods products meet the desired requirements.

The characteristic properties of the finished concrete goods products, such as, for example, their strength, are significantly determined by the raw materials and their relative amounts in the initial concrete mix as well as by the compaction during the production of the green body or fresh concrete product. For example, during compaction differences may occur that lead to different qualities. The same applies with regard to variations in the raw materials specified by the selected recipe. For example, in particular the water/cement ratio, that is also referred to as w/c value and that is determined by directly added water and the water contained in the remaining raw materials, may vary within the limits of a given recipe. Therefore, the fresh concrete consistency has to be determined prior to production and has to be followed as closely as possible. In the case of water metering devices are regularly used in the mixers in order to limit the variation of the water content.

Because variations in the manufacturing process can, however, not be eliminated completely, in view of the facts mentioned above there exists the problem that the quality of the production process can be evaluated and assessed only one month after the mixing and compaction. For this reason, faulty productions can only be discovered long after the point in time, at which it was still possible to controllingly intervene in the manufacturing process. Partly, production variations are noticed too late and losses for the producing company arise. Also, during experiments or upon changes of recipes the results can only be determined after days.

For these reasons, random tests on the fresh concrete side have been carried out sporadically in the prior art by taking individual fresh concrete products from the production process and examining them. For example, in some cases the mass or the height of fresh concrete products was measured manually or the structure was examined, and the respective single measurement value was assessed on the basis of empirical values. In most cases, it was decided subjectively by a machine operator for the fresh concrete product whether or not a product could be good. This subjective assessment often leads to increased material costs, because the machine operator tends to correct the mix such that no risk of a faulty production is taken.

Therefore, it is the object of the invention to provide a method and an apparatus for quality control of a process for producing concrete goods products, by means of which method and apparatus an assessment of the quality can be made cost effectively and quickly and the mentioned disadvantages can be eliminated. Further, the apparatus should be robust in order to be able to operate it in a harsh production environment.

The features of claims 1 and 16 serve to solve this problem. Advantageous embodiments of the method and the apparatus are the subject-matter of the respective associated dependent claims.

According to the present invention it is provided that measurements are carried out on a test fresh concrete product from an intermediate step of the production process after shaping and compaction, in order to determine measurement values on the basis of which, by means of a suitable predictive model, a value for a quality measure of the hardened concrete product can be estimated, that would result from the measured test fresh concrete product in the course of the further production process. In other words, a value is determined on the basis of measurements that are carried out in the initial phase of the production process, which value can only be measured after the completion of the production process and, thus, only at a much later time. The test fresh concrete product is simply taken from the production process at a suitable point. It may, for example, be chosen randomly as random sample.

In doing so, the measurement values determined for the test fresh concrete product comprise at least a measure of the bulk density and the gas permeability of the test fresh concrete product. As measure of the bulk density of the test fresh concrete product a geometric dimension and the mass of the test fresh concrete product are preferably measured. In case a geometric dimension and the mass are measured, the pair of values consisting of geometric dimension and mass forms the measure of the bulk density. A geometric dimension, i.e. the extension of the test fresh concrete product in a particular direction of extension, such as, for example, the height, is particularly precise in combination with the mass for determining the bulk density of the test fresh concrete product in particular if the further geometric dimensions of the test fresh concrete product, such as, for example, the width and the depth, are predetermined as set values. This is often possible because the compaction is regularly carried out from only one direction, while the further sides are predetermined by a suitable mold. For example, regularly compaction is effected from above, while from below a vibration is introduced and the sides are rigidly closed. The measured geometric dimension should preferably lie in the direction in which the compaction has been effected. However, it is, of course, also possible to completely determine the geometric dimensions of the test fresh concrete product, i.e. in the case of rectangular products the height, width and depth. Then, the mass and all geometric dimensions form in combination the measure of the bulk density.

By means of these measurement values it is possible to determine on the basis of a predetermined predictive model, that relates the measurement values of fresh concrete products from the intermediate step of the process to the quality measure of the corresponding hardened concrete products, an estimated value for a quality measure of the hardened concrete product that results or would result from the test fresh concrete product in the further course of the process. In principle, the predictive model has to be adapted for each recipe and for each given process parameter and always relates to a particular intermediate step of the process, so that the test fresh concrete product should be taken from the same point in the process with a sufficient precision. Deviations result in a reduced accuracy. Therefore, deviations are allowed to the extent in which one does not fall below the desired accuracy. In the extreme case it is also possible to provide a single predictive model for all recipes. Such a method can be carried out particularly easily, but has the disadvantage that the accuracy of the estimated values may possibly be significantly reduced. Nevertheless, such a general predictive model may be advantageous in particular applications.

The gas permeability is a measure of the structural values or also the effective porosity of the test fresh concrete product. The gas permeability has to be understood as the permeability for a particular gas or gas mixture, because in general the permeability is different for different gases or gas mixtures. Therefore, it is generally necessary for the determination of the predictive model and the later measurements to always use the same gas or gas mixture. The specific measurement method is not of importance. It is only relevant that always the same measurement method is carried out at the same method step, i.e. on comparable samples. It should be noted that also the same geometric dimension always has to be determined.

In the context of the present invention it was discovered that the above two (bulk density and gas permeability) or three (geometric dimension, mass and gas permeability) measurement values are sufficient for establishing such a predictive model. With the method according to the invention it is therefore possible to make from several combined measurement methods a statement with regard to the later quality of the finished product already in the fresh concrete phase. Thereby, the advantageous possibility is provided to detect impending faulty productions at an early stage and to act against them. Subsequent to measuring a fresh concrete product produced in a defined manner and having known and defined desired dimensions it is possible to immediately decide whether or not the green body will later achieve, for example, the necessary strength. The quality of concrete goods products, such as e.g. paving stones, can be determined advantageously immediately after the production steps that determine the final quality. In this manner, the manufacturer is able to control his production efficiently and in accordance with standards. A possible faulty protection can be excluded immediately. The present monitoring gap on the fresh concrete side is closed, and later examination results of the hardened concrete can no longer lead to unpleasant surprises. Reliability in the production and development of changed recipes is provided, a warning of possible errors is provided, and time and money is saved.

It is particularly advantageous if the geometric dimension is measured by means of an optical measurement method. A plurality of suitable measurement methods are known to the skilled person. With optical measurement methods the respective measurement value can be obtained quickly and easily. A particularly high accuracy can be obtained if the geometric dimension is measured by means of a laser.

In the case of a rectangular concrete goods product, such as, for example, a paving stone, it is preferred if the geometric dimension is the height of the test fresh concrete product. In this regard, the term height relates to the assembling position of the concrete goods product intended later on.

Further, it is preferred if the gas permeability is the permeability with respect to air. This measurement can be realized in a particularly simple, fast and cost efficient manner, because the normal atmosphere can be used and the application of special gases is not required. However, it has to be taken into consideration that an upper limit for the accuracy of the measurement exists in this case, because concrete is not inert with respect to the carbon dioxide contained in the air. If the accuracy of the measurement with air is not sufficient, gases like oxygen or nitrogen can be used.

In a preferred embodiment the gas permeability is measured by creating a pressure difference along the outer surface of the test fresh concrete product and determining a measure of the gas flow through the test fresh concrete product caused by the pressure difference. In other words, a positive pressure or negative pressure is applied to an area of the surface of the test fresh concrete product, and a quantity is measured that is characteristic of the gas pressed or sucked through the test fresh concrete product. The gas permeability only depends on the gas used and the properties of the fresh concrete product if laminar flow conditions are met and if there is no or only little interaction between the fresh concrete product and the gas. It may further be advantageous if positive pressure or negative pressure is applied to several separate areas of the surface of the fresh concrete product. In this manner inhomogeneously constructed products can be measured. For example, paving stones generally consist of a core component and a decorative component that consist of different concrete. With a suitable selection of the pressure ranges the quality of the two components can be determined separately.

It is in particular advantageous if the pressure difference is generated by applying a negative pressure to an area (or several separate areas) of the surface of the test fresh concrete product. In case a vacuum pump, that is operated with a defined pump power, is used for generating and maintaining the negative pressure, the quantity characteristic of the gas flow may be constituted advantageously by the negative pressure achieved by the vacuum pump. The higher the gas flow at a defined pump power, the worse is the vacuum achieved by the vacuum pump. Alternatively, the quantity characteristic of the gas flow may also be constituted advantageously by the time constant with which the pressure increases subsequent to generation of a defined negative pressure and deactivation of the vacuum pump. In this regard, the pressure increase occurs faster for higher gas flows. In case the pressure difference is generated by applying a negative pressure to an area of the surface of the test fresh concrete product, it is further advantageously possible to use the negative pressure for lifting and transporting the test fresh concrete product.

Preferably, the predictive model is determined empirically on the basis of a set of calibration fresh concrete products that are temporarily removed from the production process in the intermediate step and subsequently reintroduced into the production process in order to form hardened concrete products out of them. In doing so, at first the above measurement values, i.e. the bulk density and the gas permeability or the geometric dimension, the mass and the gas permeability, are determined for the calibration fresh concrete products. After the production of the hardened concrete products out of the individual calibration fresh concrete products, i.e. after 28 days, the value for the quality measure is determined for each of these hardened concrete products. Subsequently, a relationship between the values for the quality measure and the measurement values, which relationship represents the predictive model, can be determined by means of suitable methods, such as, for example, known regression methods.

It is also advantageously possible to determine the predictive model empirically on the basis of two sets of calibration fresh concrete samples that are representative of the intermediate step of the production process. The sets are chosen such that for each calibration fresh concrete product of the one set a calibration fresh concrete product is present in the other set that has been produced in exactly the same manner. The individual sets originate from the same batch and are produced with the same mixture. Further, the fresh concrete products associated with each other in pairs preferably originate from the same position in the shaping machine in order to exclude compaction differences. The one set of calibration fresh concrete products is removed from the production process in the intermediate step and is disposed of after the determination of the above measurement values. Further, for each hardened concrete product that results from the calibration fresh concrete products of the other set the value for the quality measure is determined. Subsequently, a relationship between the values for the quality measure and the measurement values, which relationship represents the predictive model, can be determined by means of suitable methods, such as, for example, known regression methods.

In a preferred embodiment the quality measure is the bulk density, the frost resistance or a strength value of the hardened concrete product. The strength value may, for example, be a tensile bending strength or a compressive strength.

By means of the possibility to determine the quality of the finished product already in an early phase of the production process it is possible in an advantageous manner to control the process for the production of concrete goods products on the basis of the difference of the value for the quality measure of the hardened concrete product, which value is determined on the basis of the predictive model for the corresponding test fresh concrete product, and a desired value for the quality measure. A closed loop control system can be formed in which the process parameters are automatically changed such that the difference between estimated value and desired value is minimized.

For performing the method according to the invention an apparatus may preferably be utilized that is adapted for carrying out measurements on the concrete goods products in an intermediate step of the process after shaping and compacting in the fresh concrete phase. For this purpose, the apparatus comprises a means for determining a measure of the bulk density of the test fresh concrete product from the intermediate step of the process and a means for determining the gas permeability of the test fresh concrete product. The means for determining a measure of the bulk density of the test fresh concrete product preferably comprises a means for determining a geometric dimension of the test fresh concrete product and a means for determining the mass of the test fresh concrete product. The pair of values provided respectively by these latter means then constitutes the measure of the bulk density. It is also possible that the means for determining a measure of the bulk density comprises further measurement means that determine additional or all geometric dimensions, wherein the additional dimensions are then incorporated into the measure of the bulk density.

Thus, in the apparatus several measurement means are combined by means of which an estimation of the quality of the finished product is possible.

This estimation may be done manually or in a separate computing means into which the measurement values provided or displayed by the apparatus are inputted. However, it is preferred that the apparatus comprises an evaluation means, that is coupled with the means for determining a measure of the bulk density and the means for determining the gas permeability or with the means for determining a geometric dimension, the means for determining the mass and the means for determining the gas permeability, and that is adapted to receive the measurement values for a test fresh concrete product from the intermediate step of the process provided by these means and to determine on the basis of a predetermined predictive model, that relates the measurement values of fresh concrete products from the intermediate step of the process with the quality measure of the corresponding hardened concrete products, an estimated value for the quality measure of the hardened concrete product that results or would result in the further course of the process from the measured test fresh concrete product. In this case, the apparatus itself may provide a signal that indicates whether the desired quality will be obtained with the current process parameters. The signal may be displayed on a suitable display means of the apparatus. A particularly simple display means consists of lights of different colors, wherein, for example, a green light indicates a sufficient quality and a red light an insufficient quality.

In a preferred embodiment the means for determining a geometric dimension is an optical measurement means with which the geometric dimension can be measured with a suitable optical measuring method. A plurality of suitable measurement means and measuring methods are known to the skilled person. By means of optical measuring methods the corresponding measurement value can be obtained very fast and simple. A particularly high accuracy can be obtained if the means for determining a geometric dimension comprises a laser by means of which the geometric dimension can be determined.

In a further preferred embodiment the means for determining a geometric dimension is adapted to determine the height of a rectangular concrete goods product. In this regard, the term height relates to the assembling position of the concrete goods product intended later on.

Further, it is preferred if the means for determining the gas permeability is adapted to determine the permeability with respect to air. Such a measurement means can be realized in a particularly simple and cost efficient manner, because the normal atmosphere can be used and the application of special gases is not necessary. The measurement can be performed very quickly with high accuracy.

In a further preferred embodiment the means for determining the gas permeability comprises a chamber, that has an opening the edges of which can be sealingly placed against an area of the outer surface of the test fresh concrete product to close the opening, a pressure generation means, with which a positive pressure or negative pressure can be generated within the chamber, and a means for determining a measure of the gas flow through the test fresh concrete product caused by the pressure difference. In other words, with the pressure generation means a positive pressure or a negative pressure can be established in a space that is one-sidedly closed in the measurement position by the test fresh concrete product. Also, the means for determining the gas permeability may comprise in an advantageous manner several separate ones of these chambers, so that it is possible to measure an inhomogeneous concrete goods product. For example, paving stones generally comprise a core component and a decorative component that consist of different concrete. With two measurement chambers it is then possible with a suitable arrangement to determine the gas permeability separately for the two components.

It is particularly preferred if the pressure generation means is adapted to generate a negative pressure in the chamber closed by the test fresh concrete product. In this case, the pressure generation means preferably comprises a vacuum pump, and the means for determining the gas permeability comprises a pressure measurement means for determining the pressure within the chamber. If the vacuum pump is operated with a defined pump power, the pressure measured by the pressure measurement means depends on the gas flow through the test fresh concrete product caused by the negative pressure. In a further preferred embodiment there is further provided a time measurement means with which the rate of the pressure increase subsequent to the deactivation of the vacuum pump can be measured. This time constant from a defined pressure level is a measure of the gas flow that can be determined easily and accurately, because it does not depend on the accurate absolute measurement of a pressure and, therefore, lower demands are made on the pressure measurement means.

It is advantageous if a transport means for lifting and transporting the test fresh concrete product is provided, wherein the chamber forms a part of the transport means and the test fresh concrete product can be lifted and transported when a negative pressure is generated within the chamber. Such a transport means can be realized particularly easily and cost effectively. With the transport means the test fresh concrete product can be taken from the production process, can be brought into a measurement position and can be disposed of or reintroduced into the production process.

It is particularly preferred if the apparatus is constructed such that the test fresh concrete product can be disposed in a single measurement position in which all required measurement values can be determined simultaneously. In this regard, the test fresh concrete product may, for example, be fixed in the measurement position by means of negative pressure in order to be able to carry out a fast and robust measurement.

It is further preferred if the evaluation means comprises a memory in which the measurement values for a set of calibration fresh concrete products from the intermediate step of the process can be stored, and if the evaluation means further comprises an input means for inputting values for the quality measure for each of the hardened concrete products, that result from the calibration fresh concrete products, or for hardened concrete products, that result from a second set of calibration fresh concrete products that was produced in the same manner as the first set. The evaluation means is adapted to store the inputted values for the quality measure in the memory and to determine a relationship between the values for the quality measure and the measurement values.

It is also possible to store in the memory different predictive models as well as further parameters specific to a particular concrete goods product. These parameters may, for example, be desired values for the width and the depth of a rectangular concrete goods product. It is then later possible to select at the evaluation means the predictive model suitable for a particular concrete goods product and the appropriate further parameters.

In the following, the invention is explained in more detail on the basis of an exemplary embodiment that is illustrated in the drawing.

FIG. 1 shows a perspective schematic view of an apparatus according to the invention for quality control of a process for producing concrete goods products.

The apparatus 1, shown in FIG. 1, for quality control of a process for producing concrete goods products comprises a transport means 2 for lifting and transporting a fresh concrete paving stone 3. The transport means 2 can be gripped with the hand by an operator at a handle 4, so that that it is possible for the operator to manually lift and transport the paving stone 3 into the measurement position in the apparatus 1. With a suitable arrangement of the apparatus 1 a paving stone 3 may be taken for measurement directly from the production process by means of the transport means 2.

For retaining the paving stone 3 the transport means 2 comprises a basis 5, the interior (not shown) of which can be (partially) evacuated via a conduit 6 for the generation of a negative pressure. For this purpose the conduit 6 is connected to a vacuum pump (not shown). In a lower end plate 7 of the basis 5 of the transport means 2 two openings 8, surrounded by a suitable seal, are provided that may be placed with their seals on the upper surface of the paving stone 3 in order to close the interior of the basis 5 by means of the paving stone 3. In this manner, following evacuation of the interior of the basis 5 the paving stone 3 is retained on the transport means 2 by the negative pressure. As compared to the also possible provision of only one opening, the provision of two openings 8 has the advantage that the measurement is more representative due to the distribution of the openings and that through the decrease in size of the individual openings the danger of a deformation of the fresh concrete product to be measured is minimized.

The apparatus 1 further comprises a weight scale 9 on which a measurement unit 10 is located. The interior of the measurement unit 10 can be (partially) evacuated via a conduit 11 for generating a negative pressure. For this purpose, just as the conduit 6 the conduit 11 is connected to a vacuum pump (not shown). In this regard, the conduits 6 and 11 may be connected to the same or to different vacuum pumps. In an upper end plate 12 of the measurement unit 10 an opening 13, surrounded by a suitable seal, is provided, on the seal of which opening the paving stone 3 retained by the transport means 2 can be placed in order to close the interior of the measurement unit 10 by means of the paving stone 3. In this manner, following evacuation of the interior of the measurement unit 10 the paving stone 3 is retained on the measurement unit 10 by the negative pressure.

This condition, in which the paving stone 3 is retained by means of negative pressure by both the transport means 2 and the measurement unit 10, is the measurement position of the paving stone 3. In this measurement position the paving stone 3 is securely fixed during the measurement. Because of this, also in a harsh production environment it is possible to carry out the measurements reliably and in a simple manner. In doing so, it is not only possible to determine the mass of the paving stone 3 by means of the weight scale 9, but it is in parallel possible to carry out several different further measurements and to determine the corresponding measurement values.

For the determination of the height of the paving stone 3 an optical distance sensor 14 is mounted on the transport means 2, which sensor may be in the case of the desire of a high accuracy, for example, a laser distance sensor and which sensor measures as a measure of the height the distance to the end plate 12 of the measurement unit 10. Further, a pressure measurement means 15 is arranged on the transport means 2, by means of which pressure measurement means the pressure within the interior of the basis 5 of the transport means 2 can be measured. Similarly, a pressure measurement means (not shown) is provided in the measurement unit 10, by means of which pressure measurement means the pressure within the interior of the measurement unit 10 can be measured. If the vacuum pump is or the vacuum pumps are, as the case may be, operated with a defined pump power, the pressures measured by the pressure measurement means of the transport means 2 and the measurement unit 10 are characteristic of the air flows through the paving stone 3 caused by the negative pressures.

The signals provided by the pressure measurement means 15 and the laser distance sensor 14 are supplied via electric lines, that may be integrated into the conduit 6, or wirelessly to an evaluation and control unit 16. In a similar manner, the signals provided by the weight scale 9 and the pressure measurement means of the measurement unit 10 are supplied via electric lines, that may be integrated into the conduit 11, or wirelessly to the evaluation and control unit 16. The unit 16, through which the operation of the apparatus 1 is controlled, comprises a processor and a memory coupled to the processor, by means of which the received signals can be evaluated using a suitable predictive model for determining a value for a quality measure of the finished paving stone that would result from the fresh concrete paving stone 3 after completion of the production process. The unit 16 preferably comprises suitable input means for inputting parameters for the evaluation.

Before the apparatus 1 is utilized in the production process of a particular paving stone product the unit 16 has to be initialized with the appropriate parameters for the evaluation. For this purpose the production process of the paving stone product is carried out for a test batch. In a defined intermediate step in the fresh concrete phase of the production process after shaping and compacting in a stone shaping machine several fresh concrete paving stones 3 are seized one after the other by means of the transport means 2 and removed from the production process. The individual fresh concrete paving stones 3 are transported to the apparatus 1 and are placed in the measurement position in order to carry out the measurements described above and to determine the corresponding measurement values for each fresh concrete paving stone 3. The measurement values are stored in the memory of the unit 16 in such a manner that a later association with the individual fresh concrete paving stones 3 is possible. After its measurement and the termination of the negative pressure in the measurement unit 10 each fresh concrete paving stone 3 is trans-ported away from its measurement position by means of the transport means 2 and is reintroduced into the production process. In doing so, the fresh concrete paving stone 3 is released from the transport means 2 by terminating the negative pressure in the basis 5. Alternatively, the measured fresh concrete paving stones 3 may also be disposed of, which has to be done if the measured fresh concrete paving stones 3 experience modifications during the measurement. In the case of the disposal, for each measured fresh concrete paving stone 3 a fresh concrete paving stone that is as identical as possible and that passes completely through the production process has to be present for the further method. Such fresh concrete paving stones with almost identical properties can be produced within the same batch with an identical mix and at identical locations in the shaping machine.

The measured fresh concrete paving stones 3 or the fresh concrete paving stones 3 that are as identical as possible, as the case may be, pass completely through the remainder of the production process. Subsequently, i.e. approximately 28 days after the measurement, the hardened concrete paving stones that have been produced from the measured fresh concrete paving stones 3 or the fresh concrete paving stones 3 that are as identical as possible, as the case may be, are examined with respect to their quality by determining values for one or several quality measures such as, for example, the strength or the bulk density. These measurements may be carried out by means of separate measurement devices. However, it is also possible to integrate corresponding measurement devices into the apparatus 1. In any case, the measured quality values are provided to the unit 16, for example by manually inputting them, and stored in the memory of the unit 16 in such a manner that they are associated with the measurement values of the respective corresponding fresh concrete paving stone 3. The processor of the unit 16 is then able to calculate by means of an appropriate regression method a predictive model that relates the measurement values of the fresh concrete paving stones 3 to the quality values of the corresponding hardened concrete paving stones. The measured fresh concrete paving stones and, if applicable, the fresh concrete paving stones that are as identical as possible constitute respectively a set of calibration paving stones.

In general, this initialization has to be repeated for each individual concrete goods product, i.e. for a particular recipe and particular further process parameters, because in general the predictive models will differ from each other. However, in practice it is possible to divide the various concrete goods products into groups with sufficiently similar properties and to use for each group a single predictive model that provides a sufficient accuracy for all group members. In the extreme case it is also possible to use a single general predictive model for all concrete products. Even though the accuracy is possibly significantly reduced in this case, such a predictive model may be sufficient for simple and cost effective estimates. A corresponding apparatus could be simplified in its construction.

The initialization may be carried out by the operator himself or also by the manufacturer. For example, the manufacturer may pre-initialize the apparatus for a plurality of typical concrete goods products.

The different predictive models are stored in the memory of the unit 16. Once the unit 16 is initialized for a particular concrete goods product it is possible in this manner to select the appropriate predictive model at the unit 16. Then, the quality of the production process can be controlled for, for example, a particular paving stone product by sporadically taking with the transport unit 3 test fresh concrete stones from the process in the intermediate step that was used for establishing the predictive model. For this purpose, the operator simply has to place the transport means 2 on the test fresh concrete stone 3 and to activate the vacuum pump for generating negative pressure in the basis 5. After arrangement of the test fresh concrete stone 3 in the measurement position in the apparatus 1 the various measurement values are automatically determined in parallel and provided to the unit 16. The unit 16 then calculates on the basis of the appropriate predictive model a value for one or several quality measures of the finished product that would result from the test fresh concrete stone 3 if the test fresh concrete stone 3 would be reintroduced into the production process. This reintroduction is in fact easily possible if the measurements are carried out very quickly and the test fresh concrete stone 3 is not modified. If the test fresh concrete stone 3 is reintroduced into the production process it is advantageous if values for the quality measures are measured on the corresponding finished product and provided to the unit 16. In this manner the unit 16 is able to further improve the predictive model during normal operation. The same may also be achieved if for the test fresh concrete stone 3 a further test fresh concrete stone 3 exists that is as identical as possible and that has been produced in the manner mentioned above and runs completely through the production process.

The apparatus may also be constructed even more compact by installing a load cell into the transport means 2 instead of the provision of the weight scale 9. The mass is then determined while the test fresh concrete product depends from the trans-port means. If the unit 16 is also integrated into the trans-port means 2 or the measurement values are provided wirelessly to a separate unit 16, the entire apparatus can be constructed as a portable apparatus, possibly with the exception of the vacuum pumps.

The invention claimed is:

1. A method for quality control of a process for producing concrete goods products, wherein the quality control is carried out on the basis of measurements that are performed on the concrete goods products in an intermediate step of the process after shaping and compacting in the fresh concrete phase, wherein the method comprises:

determining measurement values on a test fresh concrete product from the intermediate step of the process, wherein the measurement values comprise a measure of the bulk density and the gas permeability of the test fresh concrete product, and determining an estimated value for a quality measure of the hardened concrete product, that results in the further course of the process from the test fresh concrete product, on the basis of a predetermined predictive model that relates the measurement values of fresh concrete products from the intermediate step of the process to the quality measure of the corresponding hardened concrete products.

2. The method according to claim 1, wherein a geometric dimension and the mass of the test fresh concrete product is determined as the measure of the bulk density of the test fresh concrete product.

3. The method according to claim 2, wherein the geometric dimension is determined by means of an optical measurement method.

4. The method according to claim 3, wherein the geometric dimension is measured by means of a laser.

5. The method according to claim 2, wherein the concrete goods product is rectangular and the geometric dimension is the height of the test fresh concrete product.

6. The method according to claim 1, wherein the gas permeability is the permeability with respect to air.

7. The method according to claim 1, wherein the gas permeability is measured by establishing a pressure difference along the outer surface of the test fresh concrete product and determining a measure of the gas flow through the test fresh concrete product caused by the pressure difference.

8. The method according to claim 7, wherein the pressure difference is created by applying a negative pressure to an area of the surface of the test fresh concrete product.

9. The method according to claim 8, wherein the negative pressure is generated and maintained by means of a vacuum pump with a predetermined pump power and wherein the negative pressure obtained by the vacuum pump is measured as a measure of the gas flow.

10. The method according to claim 8, wherein the negative pressure is generated by means of a vacuum pump and wherein the rate of the pressure increase following deactivation of the vacuum pump is measured as a measure of the gas flow.

11. The method according to claim 8, wherein the negative pressure is used to lift and transport the test fresh concrete product.

12. The method according to claim 1, wherein the predictive model is determined empirically by determining the measurement values for a set of calibration fresh concrete products from the intermediate step of the process, determining the value for the quality measure for each of the hardened concrete products that result from the calibration fresh concrete products, and determining a relationship between the values for the quality measure and the measurement values.

13. The method according to claim 1, wherein the predictive model is determined empirically by providing two sets of calibration fresh concrete products from the intermediate step of the process, wherein for each calibration fresh concrete product of the one set a calibration fresh concrete product is present in the other set which product has been produced in exactly the same manner, and by determining the measurement values for one set of calibration fresh concrete products from the intermediate step of the process and determining for each of the hardened concrete products, that result from the calibration fresh concrete products of the other set, the value for the quality measure and determining a relationship between the values for the quality measure and measurement values.

14. The method according to claim 1, wherein the quality measure is the bulk density, the frost resistance or a strength value of the hardened concrete product.

15. The method according to claim 1, wherein the process for producing concrete goods products is controlled on the basis of the difference of a value for the quality measure of the corresponding hardened concrete product, which value is determined on the basis of the predictive model for the test fresh concrete product, and a desired value for the quality measure.

16. An apparatus for quality control of a process for producing concrete goods products, which apparatus is adapted to carry out measurements on the concrete goods products in an intermediate step of the process after shaping and compacting in the fresh concrete phase, wherein the apparatus comprises:
  a means for determining a measure of the bulk density of a test fresh concrete product from the intermediate step of the process,
  a means for determining the gas permeability of the test fresh concrete product, and
  an evaluation means that is coupled to the means for determining a measure of the bulk density and the means for determining the gas permeability, and that is adapted to receive the measurement values for a test fresh concrete product from the intermediate step of the process provided by these means and to determine on the basis of a predetermined predictive model, that relates the measurement values of fresh concrete products from the intermediate step of the process to a quality measure of the corresponding hardened concrete products, an estimated value for the quality measure of the hardened concrete product that results in the further course of the process from the measured test fresh concrete product.

17. The apparatus according to claim 16, wherein the means for determining a measure of the bulk density of the test fresh concrete product comprises a means for determining a geometric dimension of the test fresh concrete product and a means for determining the mass of the test fresh concrete product.

18. The apparatus according to claim 17, wherein the means for determining a geometric dimension is an optical measurement means by means of which the geometric dimension can be measured with a suitable optical measurement method.

19. The apparatus according to claim 18, wherein the means for determining a geometric dimension comprises a laser by means of which the geometric dimension can be determined.

20. The apparatus according to claim 17, wherein the means for determining a geometric dimension is adapted to determine the height of a rectangular concrete goods product.

21. The apparatus according to claim 16, wherein the means for determining the gas permeability is adapted to determine the permeability with respect to air.

22. The apparatus according to claim 16, wherein the means for determining the gas permeability comprises a chamber, that has an opening the edges of which can be sealingly placed against an area of the outer surface of the test fresh concrete product in order to close the opening, and wherein the means for determining the gas permeability further comprises a pressure generation means, with which a positive pressure or a negative pressure can be generated within the chamber, and a means for determining a measure of the gas flow through the test fresh concrete product caused by the pressure difference.

23. The apparatus according to claim 22, wherein the pressure generation means is adapted to generate a negative pressure within the chamber closed by the test fresh concrete product.

24. The apparatus according to claim 23, wherein the pressure generation means comprises a vacuum pump and wherein the means for determining the gas permeability comprises a pressure measurement means for determining the pressure within the chamber.

25. The apparatus according to claim 24, that further comprises a time measurement means with which the rate of the pressure increase following deactivation of the vacuum pump can be measured.

26. The apparatus according to claim 23, further comprising a transport means for lifting and transporting the test fresh concrete product, wherein the chamber constitutes a part of the transport means and the test fresh concrete product can be lifted and transported when a negative pressure is generated within the chamber.

27. The apparatus according to claim 16, wherein the evaluation means comprises a memory in which the measurement values for a set of calibration fresh concrete products from the intermediate step of the process can be stored, and that further comprises an input means for inputting values for the quality measure for each of the hardened concrete products, that result from the calibration fresh concrete products, or for hardened concrete products, that result from a second set of calibration fresh concrete products that has been produced in the same manner as the first set, wherein the evaluation means is adapted to store the inputted values for the quality measure in the memory and to determine a relationship between the values for the quality measure and the measurement values.

* * * * *